(12) United States Patent
Palmerton et al.

(10) Patent No.: US 6,524,307 B1
(45) Date of Patent: Feb. 25, 2003

(54) SMOKE EVACUATION APPARATUS

(75) Inventors: Christopher A. Palmerton, Clarence, NY (US); Daniel R. Palmerton, Amherst, NY (US); Earnest R. Moehlau, Amherst, NY (US); Robert O. Dean, Buffalo, NY (US)

(73) Assignee: Medtek Devices, Inc., Amherst, NY (US)

( * ) Notice: Subject to any disclaimer, the term of this patent is extended or adjusted under 35 U.S.C. 154(b) by 0 days.

(21) Appl. No.: 09/972,423

(22) Filed: Oct. 5, 2001

(51) Int. Cl.$^7$ ................................................ A61B 18/18
(52) U.S. Cl. ............................ 606/41; 606/49; 604/22; 604/35
(58) Field of Search .................. 606/38–41, 45, 606/46, 48–50; 604/21, 22, 35

(56) References Cited

U.S. PATENT DOCUMENTS

| | | |
|---|---|---|
| 3,825,004 A | 7/1974 | Durden III |
| 3,828,780 A | 8/1974 | Morrison, Jr. |
| 3,906,955 A | 9/1975 | Roberts |
| 3,974,833 A | 8/1976 | Durden III |
| 4,307,720 A | 12/1981 | Weber, Jr. |
| 4,562,838 A | 1/1986 | Walker |
| 4,719,914 A | 1/1988 | Johnson |
| 4,735,603 A | 4/1988 | Goodson et al. |
| 4,919,129 A | 4/1990 | Weber, Jr. et al. |
| 5,085,657 A | 2/1992 | Ben-Simhon |
| 5,133,714 A | 7/1992 | Beane |
| 5,192,267 A | 3/1993 | Shapira et al. |
| 5,217,457 A | 6/1993 | Delahuerga et al. |
| 5,224,944 A | 7/1993 | Elliott |
| 5,234,428 A | 8/1993 | Kaufman |
| 5,269,781 A | 12/1993 | Hewell III |
| 5,431,650 A | 7/1995 | Cosmescu |
| 5,451,222 A | 9/1995 | De Maagd et al. |
| 5,451,223 A | 9/1995 | Ben-Simhon |
| D384,148 S | 9/1997 | Monson |
| 5,674,219 A | 10/1997 | Monson et al. |
| 5,836,944 A | 11/1998 | Cosmescu |
| D426,883 S | 6/2000 | Berman et al. |
| 6,142,995 A | 11/2000 | Cosmescu |
| 6,146,353 A | 11/2000 | Platt, Jr. |

OTHER PUBLICATIONS

Implantech Associates, Inc., The SE–100 Smoke Aspiration Tip, published prior to Oct. 2001, Ventura, CA.
I. C. Medical, Inc., Crystal Vision Model 350D, published prior to Oct. 2001, Glendale, AZ.
Lina Medical CML ApS, Lina Smoke Evacuation System, Mar. 1999, Glostrup, Denmark.
ECRI, ESU–Pencil–Based Smoke Evacuation Wands, Health Devices, vol. 26, No. 4, pp. 173, 174(partial), Plymonth Meeting, PA, Apr. 1997.

Primary Examiner—Michael Peffley
(74) Attorney, Agent, or Firm—Simpson & Simpson, PLLC

(57) ABSTRACT

A combined smoke evacuation and filter apparatus adapted to receive and hold a surgical device which may produce smoke such as a cauterization pencil or a laser device, and which apparatus can be connected to a vacuum source. The apparatus includes a unitary holder formed of elastic material, a suction tube carrying the power line of the device, a tubular plastic back end piece connecting the holder to the suction tube, and a filter housing at an end of the suction tube. The filter housing contains a four stage filter and a casual liquid collector. The unitary holder has a cradle, a conically shaped portion, and an oval shaped lumen located below the cradle for carrying the smoke to the end piece. The tubular back end piece is provided with a retaining fork which bears against the proximal end of the device, the elastic holder being stretched when the parts are assembled.

17 Claims, 7 Drawing Sheets

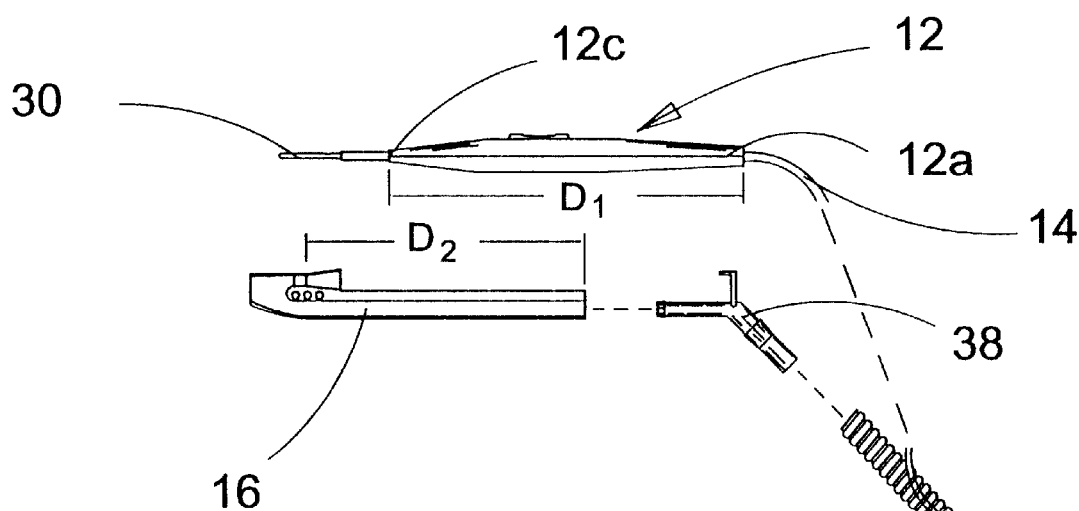
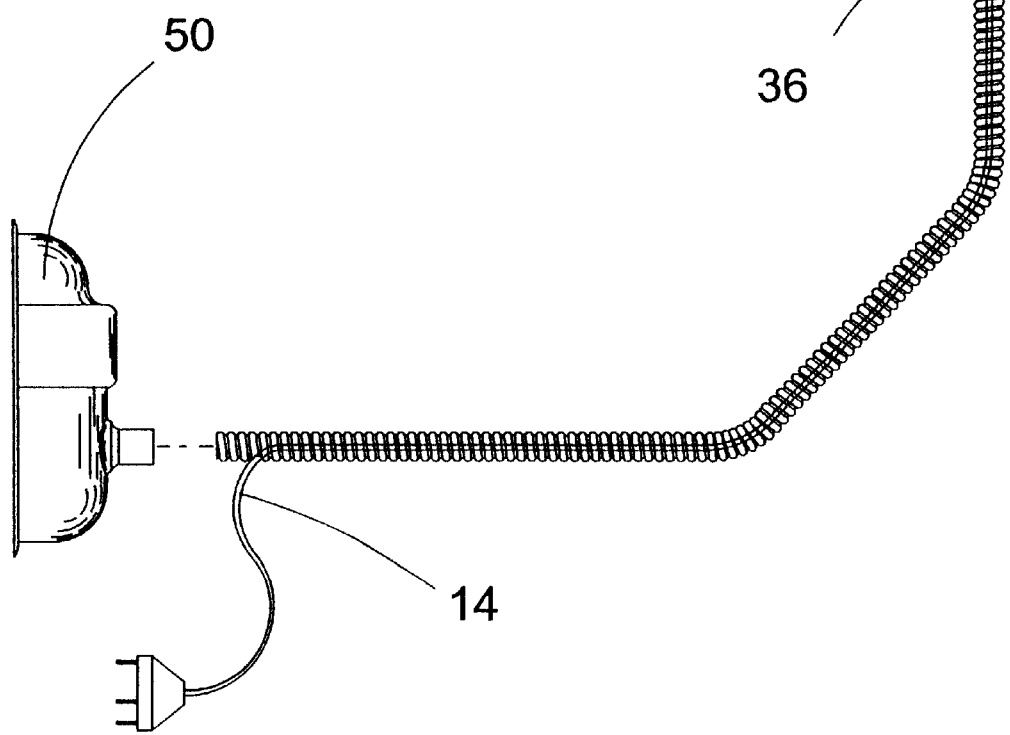
Fig. 2

SMOKE EVACUATION APPARATUS

TECHNICAL FIELD

The present invention relates to a smoke evacuation apparatus shaped to receive a surgical device which may create smoke, and which can be connected to a vacuum source for evacuation of smoke. More particularly, the present invention relates to a combined smoke evacuation and filter apparatus which may be disposed of after up to four hours of use, the apparatus including a unitary holder formed of elastic silicone adapted to receive surgical device which may create smoke, a suction tube carrying the power source of the device, a tubular back end piece connecting the holder to the suction tube, and a filter housing at an end of the suction tube, the filter housing containing a four stage filter and a casual liquid collector.

BACKGROUND OF THE INVENTION

Surgical smoke and aerosol, or plume, is created when energy is imparted to tissue cells during surgery. For example, when laser or electrosurgical energy is delivered to a cell, heat is created. The heat vaporizes the intracellular fluid, which increases the pressure inside the cell and eventually causes the cell membrane to burst. When this happens, a plume of smoke containing mostly water vapor is released into the atmosphere of the operating room or doctor's office. At the same time, the intense heat created chars the protein and other organic matter within the cell, and causes thermal necrosis in adjacent cells. The charring of cells, like grilling on a barbecue, releases other harmful contaminants, such as carbonized cell fragments and gaseous hydrocarbons.

Surgical smoke and aerosol is typically produced during procedures utilizing lasers and electrosurgical equipment. Other sources of smoke may be dental drill or harmonic tools. The power sources for these devices are typically electrical leads or air lines.

Research shows that both laser and electrosurgical smoke and aerosol have very similar makeup. These small particles and gases are potentially hazardous if inhaled. If they are not evacuated, they become airborne and can be inhaled.

Reports of health care workers becoming infected with HIV through injuries with sharp objects and exposure to blood and other body fluids have sparked concern about the possibility of the transmission of HIV or other bloodborne pathogens through the aerosols produced by powered surgical instruments.

Surgical smoke and aerosol generated in an open operating room environment is absorbed primarily via the respiratory tract, but the harmful components of surgical smoke and aerosol can also be absorbed by the skin and mucous membranes.

Exactly what is in surgical smoke and aerosol? The potential hazards can vary, depending primarily upon what energy source is used to create the smoke and the tissue or substance being altered or aerosolized. Generally, the composition of surgical smoke and aerosol generated by a laser or electrosurgical procedure is 95% water vapor and 5% other matter. It is this "other matter" that is potentially hazardous to the health of surgical personnel and their patients. The hazards fall into two broad categories: biological and chemical.

Potentially harmful biological components include infectious bacteria and viruses, either intact or fragmented. The potentially toxic chemicals in surgical smoke and aerosol include proven toxins, mutagens, carcinogens, and allergens. The average size of the particles contained in surgical smoke and aerosol is 0.31 microns ($\mu$m), with a range of 0.10 to 0.80 $\mu$m. This is also the most dangerous particle size, because it is the optimal size to be deposited in the lower respiratory tract. The sizes of some of the most significant human pathogens are as follows:

Hepatitis B virus, 0.042 $\mu$m

Human Immunodeficiency Virus, 0.180 $\mu$m

Human Papilloma Virus, 0.045 $\mu$m

Mycobacterium tuberculosis, 0.500 $\mu$m

The actual number of particles present in surgical smoke and aerosol can vary depending on the type of surgery and its duration, but generally range from 1,000,000 to 1,000,000,000 particles. Researchers have collected intact cells, cell parts, and intact viral DNA from the plume. Viable bacteria have been cultured from surgical plume. Mycobacteria have also been isolated in smoke plume and aerosols, including Mycobacterium tuberculosis. The viruses of greatest concern to users of lasers, electrosurgery, and powered surgical instruments are the Human Immunodeficiency Virus (HIV) and Human Papilloma Virus (HPV).

Surgical smoke and aerosol has been shown to contain a wide variety of toxic chemical byproducts. An example is toluene. This industrial solvent is irritating to the eyes, nose, and respiratory tract. Inhalation of high concentrations produces a narcotic effect, sometimes leading to coma as well as liver and kidney damage.

There seems to be no doubt that potentially harmful biological and chemical materials are contained in surgical smoke and aerosol.

Surgical smoke and aerosol occludes the vision of the surgeon and the rest of the team in both open and minimally invasive surgical procedures. This lack of visibility can lengthen the procedure, adding to costly operating room time and subjecting the patient to increased time under anesthesia. Furthermore, the smoke will hamper the performance of laser devices.

Aesthetically, the odor of surgical smoke and aerosol is extremely offensive to surgeons, nurses, patients, and others in the operating room. It attaches to hair, surgical attire, and any exposed skin surfaces. It can irritate the eyes and cause nausea and vomiting. There is also evidence that the unpleasant smell heightens patient anxiety.

Increasing recognition of the potentially infectious and toxic effects of surgical smoke and aerosol exposure has led to the development and implementation of smoke evacuation systems. Thus, the most effective way of protecting personnel and patients from inhaling the harmful components of surgical smoke and aerosol is to use a system for suctioning the smoke, which system preferably is provided with a high-efficiency filter.

A smoke evacuator is basically a vacuum pump with one or more filters designed to evacuate surgical smoke and aerosol from the operative site, filter out essentially all of the contaminants, and return the filtered air to the operating room.

The smoke evacuator's filter system removes particles from the suctioned airstream at the surgical site. The different types of filters that may be found in hospital-grade smoke evacuators are as follows:

Prefilter. Prefilters made of sponge or wire grating are used to capture objects (e.g., cotton), fluid, or gross particulates that can be accidentally sucked into the airstream and subsequently damage the high-efficiency filter or the evacuator pump.

A HEPA or ULPA filter. A High Efficiency Particulate Air (HEPA) filter captures 99.97% of dioctylphthalate particles 0.3 µm in diameter. Three particles out of 10,000 may pass through the filter. An Ultra Low Penetration Air (ULPA) filter is designed to capture very small particles and organisms. Research has shown that pathogens such as HIV, HPV, and HBV particles are found attached to droplet nuclei, and that the total size of the particle is significantly larger than the 0.1 µm particles that an ULPA filter is designed to capture.

Activated charcoal filter. Activated charcoal filters adsorb odors and gaseous hydrocarbons from the waste exhaust. Activated charcoal filters are a carbon-based compound that is baked at high temperatures without the presence of oxygen. This process "activates" the charcoal by removing the organic compounds and leaving only the carbon matrix behind. Through this process, the carbon granules become full of active sites where organic molecules may be captured without changing the carbon structure. The largest user of active sites in activated charcoal is water vapor.

Finally, a final filter is typically employed to remove activated carbon "fines."

Research confirms the effectiveness of these filter media in screening out harmful contaminants. To extend their use, filters may be impregnated with an antimicrobial agent, to inhibit the growth and reproduction of microorganisms that become trapped in the filter.

The prior art also teaches that a suction canister may be installed upstream of the filter to receive any liquids suctioned during a procedure.

Various smoke evacuation systems are known in the art. These include smoke evacuation units where filtered air is recirculated into the room, or centralized vacuum systems where smoke is vacuumed into a centrally maintained filter system. The ability of either a smoke evacuator system to collect plume depends on the volume of air removed from the surgical site, the velocity of the air entering the nozzle, and the static suction of the blower/motor of a vacuum smoke evacuation system. The velocity of the airstream is proportional to the air flow through the evacuator and inversely proportional to the diameter of the nozzle opening. The vacuum motor creates a vortex that overcomes the particles' momentum, changing their direction so that they are drawn into the nozzle, through the hose, and through the filter.

When the nozzle of a smoke evacuation unit is held more than 2 inches from the site, its collection efficiency declines or decreases rapidly, especially if external air flow is present in a direction away from the nozzle flow and the evacuator flow is low. Therefore, various integrated evacuation electrosurgical pencils have been developed.

Durden U.S. Pat. No. 3,825,004 discloses a combined disposable cauterization pencil and smoke evacuation unit, see FIG. 19. The pencil is integrated into a specially shaped plastic housing which is contoured to provide "deft and positive" use of the device, the pencil including an elongated metallic electrode tube. The electrical wire for the pencil is carried by the smoke evacuation tube in parallel relationship, see FIGS. 18 and 20.

Durden U.S. Pat. No. 3,974,833 is a continuation-in-part and further discloses in FIGS. 21–24 a "frangible membrane" which is breachable to vary the suction.

Cosmescu U.S. Pat. Nos. 5,836,944 and 6,142,995 disclose a conventional pencil and a novel removable shroud which is used as a smoke evacuation unit, see FIGS. 8A–F. The shroud has a cut away portion to provide an access for the pencil switch. The smoke evacuation tube is semi-circular. It is a feature of this patent that the nozzle 412 is tapered to create a tapered passageway which creates an exhaust vortex near the operation site.

Monson et al U.S. Pat. No. 5,674,219 discloses a one-time use combined pencil holder, smoke filter, and tube which extends from the holder to the filter, see FIG. 4, and col. 9, line 31. The pencil holder is provided with a fork 72 which engages the rear of the pencil, the fork being carried by a ratchet mechanism. The holder has a tubular nose portion which receives the distal end of the pencil. The filter includes a particulate filter for filtering particles in the 0.2 to 0.7 µm range and a granular activated charcoal adsorption bed. It is a feature of this patent that the nozzle has a nose provided with a specific radius which reduces noise.

Maagd et al U.S. Pat. No. 5,451,222 discloses a smoke evacuation unit including a suction unit 38 having a removable filter 52.

Delahuerga U.S. Pat. No. 5,217,457 teaches an electric knife with an attachable shroud that works in reverse in that the shroud allows filtered (via filter 24, FIG. 20) inert gas to surround the blade.

Other prior art U.S. Patents include U.S. Pat. Nos. 3,828,780, 4,562,838, 4,735,603, 5,085,657, 5,133,714, 5,451,223, and 6,146,353. Design patents include U.S. Pat. Nos. 384,148 and 426,833.

OBJECTS AND SUMMARY OF THE INVENTION

It is an object of the present invention to provide a smoke evacuation apparatus suitable for use in open procedures which will be comfortable to use and which will provide a high level of protection.

More particularly, it is an object of the present invention to provide a smoke evacuation apparatus shaped to receive a surgical device which may create smoke, such as an electrically operated laser or electrosurgical device, and which apparatus can be connected to a vacuum system, the apparatus including an elongated unitary holder formed of an elastic material such as silicone, the holder having a cradle for receiving a device, a lumen below the cradle, a conical portion for receiving the distal end of the device, the apparatus further including a suction tube, and a tubular substantially rigid back end piece interconnecting the lumen with the suction tube, the tubular back end piece being provided with a retaining fork which bears against the proximal end of the device, the distal end being snugly received within the conical portion, and the elastic device holder being stretched when the parts are assembled to cause the device to be retained.

It is a further object of the present invention to provide an apparatus of the type set forth above wherein a power source (such as an electrical lead) for the device passes through the suction tube, the power source entering the suction tube adjacent one end and exiting the suction tube adjacent the other end.

Another object of the present invention is to provide an apparatus of the type set forth above wherein the tubular substantially rigid back end piece is formed at an angle of about 135° to cause the suction tube and power source to lay comfortably over the user's wrist.

A further object of the present invention is to provide a combined smoke evacuation and filter apparatus shaped to receive an electrically operated laser or electrosurgical device, which apparatus can be connected to a vacuum smoke evacuation system, the apparatus including a unitary holder formed of elastic material to facilitate holding of the device, the unitary holder including a U-shaped pencil cradle which extends from the proximal end, a conically shaped portion adjacent the distal end of the cradle, an oval shaped lumen located just below the cradle and the conically shaped portion, and an elongated tubular opening at the distal end through which smoke may pass; a suction tube; a tubular substantially rigid back end piece connecting the oval shaped lumen of the pencil holder to the suction tube; and a filter housing at an end of the suction tube, which filter housing may be connected to a vacuum source so that smoke and other debris may be vacuumed into the elongated tubular opening at the distal end of the unitary pencil holder, through the lumen, through the tubular back end piece, through the suction tube, and then through the filter housing, which filter housing contains one or more filters.

A further object of the present invention is to provide a combined smoke evacuation and filter apparatus of the type set forth above wherein the tubular back end piece is provided with a retaining fork which bears against the proximal end of the device, the distal end being snugly received within the conical portion, the holder being stretched when the parts are assembled to cause the device to be retained.

A still further object of the present invention is to provide a combined smoke evacuation and filter apparatus of the type set forth above wherein suction tube carries the electrical lead of the device.

Yet another object of the present invention is to provide a combined smoke evacuation and filter apparatus of the type set forth above wherein the filter housing contains a four stage filter and a casual liquid collector.

A further object of the present invention is to provide a combined smoke and filter apparatus of the type set forth above wherein the four stage filter includes a prefilter to remove gross particulates and moisture, an ULPA filter to remove fine particulates and microorganisms, an activated carbon filter to remove odors and organic gases, and a final filter to remove activated carbon "fines."

Another object of this invention is to provide a combined smoke evacuation and filter apparatus as set forth above wherein a membrane is formed in the narrow distal end of the conical portion and may be pierced by an electrode of a cauterization pencil when it is inserted, thus providing a leak barrier, assuring that the vacuumed smoke remains in the lumen and suction tube to be safely filtered by the filter device that is attached to a vacuum supply.

A still further object of this invention is to provide a combined smoke evacuation and filter apparatus as set forth above wherein the apparatus is designed for a single use.

The above objects and other objects and advantages of this invention will become more apparent after a consideration of the following detailed description taken in conjunction with the accompanying drawings which illustrate a preferred mode of this invention.

BRIEF DESCRIPTION OF THE DRAWINGS

FIG. 1A is an enlarged portion of FIG. 1.

FIG. 2 is a view similar to FIG. 1, but showing the parts in a disassembled condition.

DETAILED DESCRIPTION

Figure 1:
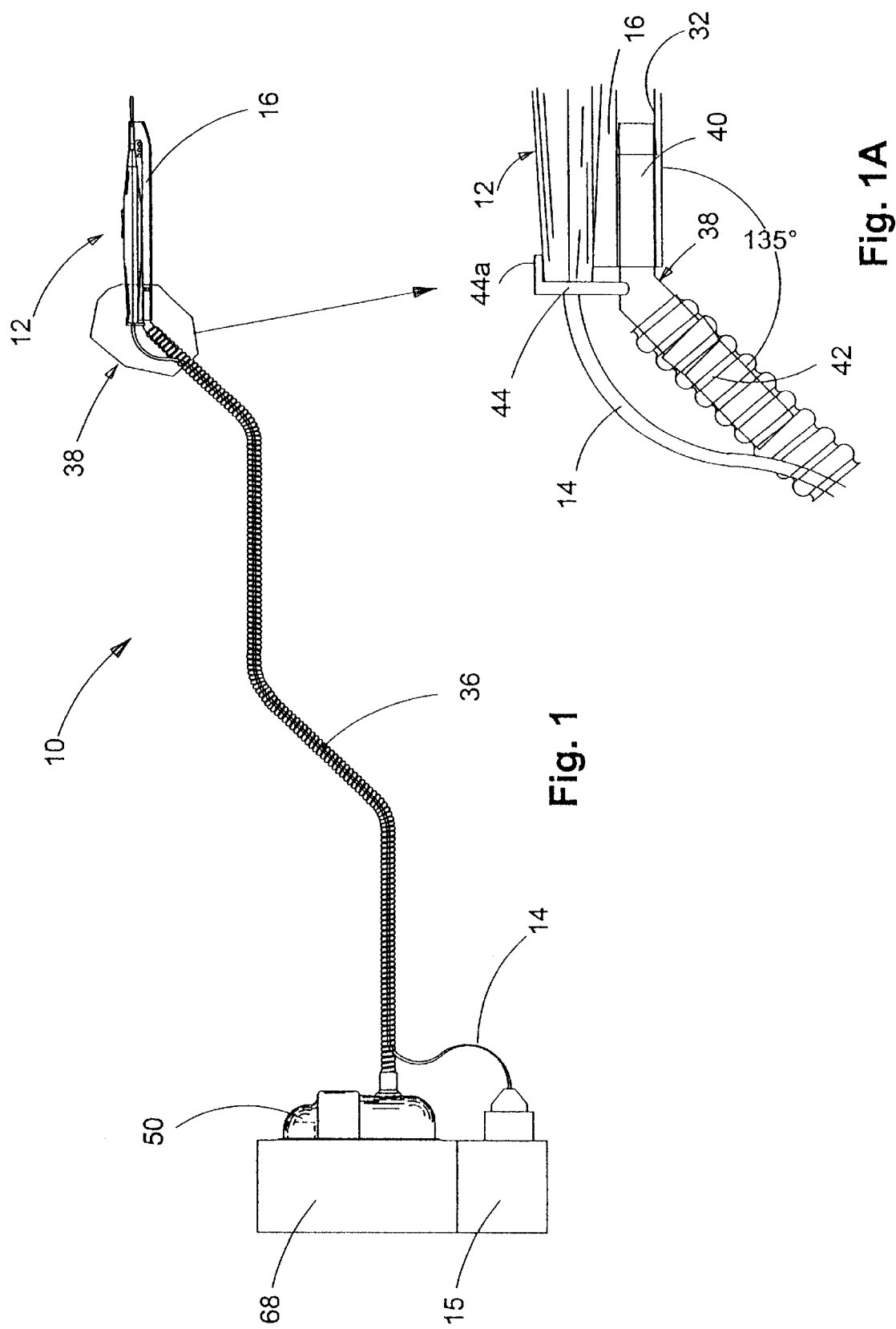
FIG. 1 is an overall view of the smoke evacuation and filter apparatus of the present invention, the apparatus being connected to a vacuum source and to an electrical supply.

With reference initially to FIG. 1 the combined smoke evacuation and filter apparatus of the present invention is indicated generally at 10. The apparatus of this invention is designed to be used with electrically operated laser devices or with electrosurgical devices such as cauterization pencils, best shown in FIG. 2, and indicated generally at 12. Alternatively, the apparatus of the present invention may be used with argon beam coagulation pencils (not shown). The devices typically are powered through one or more electrical leads 14 connected to a suitable power supply 15. The apparatus of this invention is designed for a single use when used in a surgical suite of up to 4 hours, at which time it may be discarded. By discarding it, it makes regulatory compliance easier and cheaper, it also makes the system safer, thereby reducing insurance costs.

Figure 3:
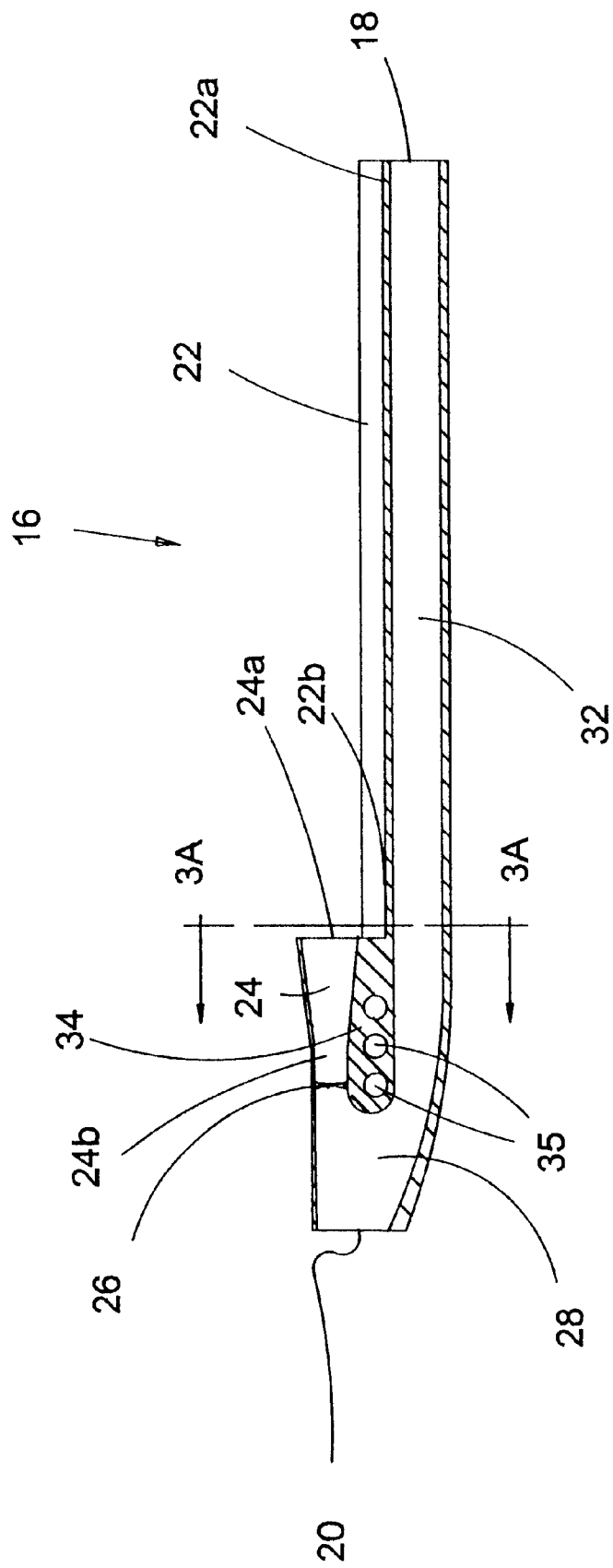
FIG. 3 is a sectional view of the elongated unitary holder of this invention.

A primary component of the smoke evacuation apparatus of this invention is an elongated unitary holder, indicated generally at 16 in FIG. 3. The holder is formed of an elastic material, preferably silicone, or an equivalent material such as PVC. There are several advantages to forming the holder of a soft elastic material, such as silicone, a principal one being that the silicone material makes it easier to grasp the device and holder by the user, who may be wearing latex gloves. Furthermore, the silicone material is atraumatic to tissue. As the material is elastic, it will conform to most devices. Also, it is less tiring to use because it conforms to the user's hand. Other advantages will be apparent to those skilled in the art.

Figure 4:
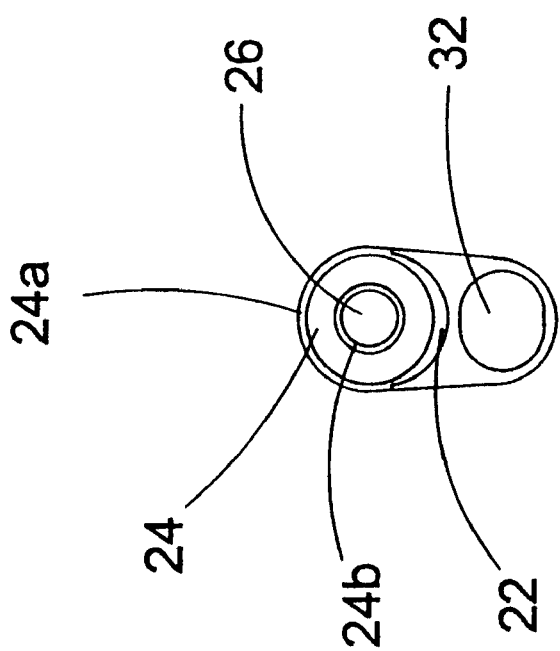
FIG. 4 is an end view of the pencil holder shown in FIG. 3, this view being taken from the right side.
Figure 3A:
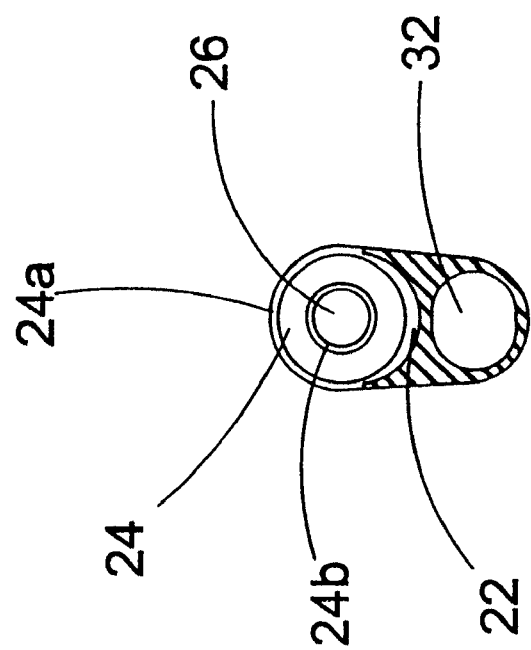
FIG. 3A is a sectional view taken generally along the line 3A—3A in FIG. 3.
Figure 5:
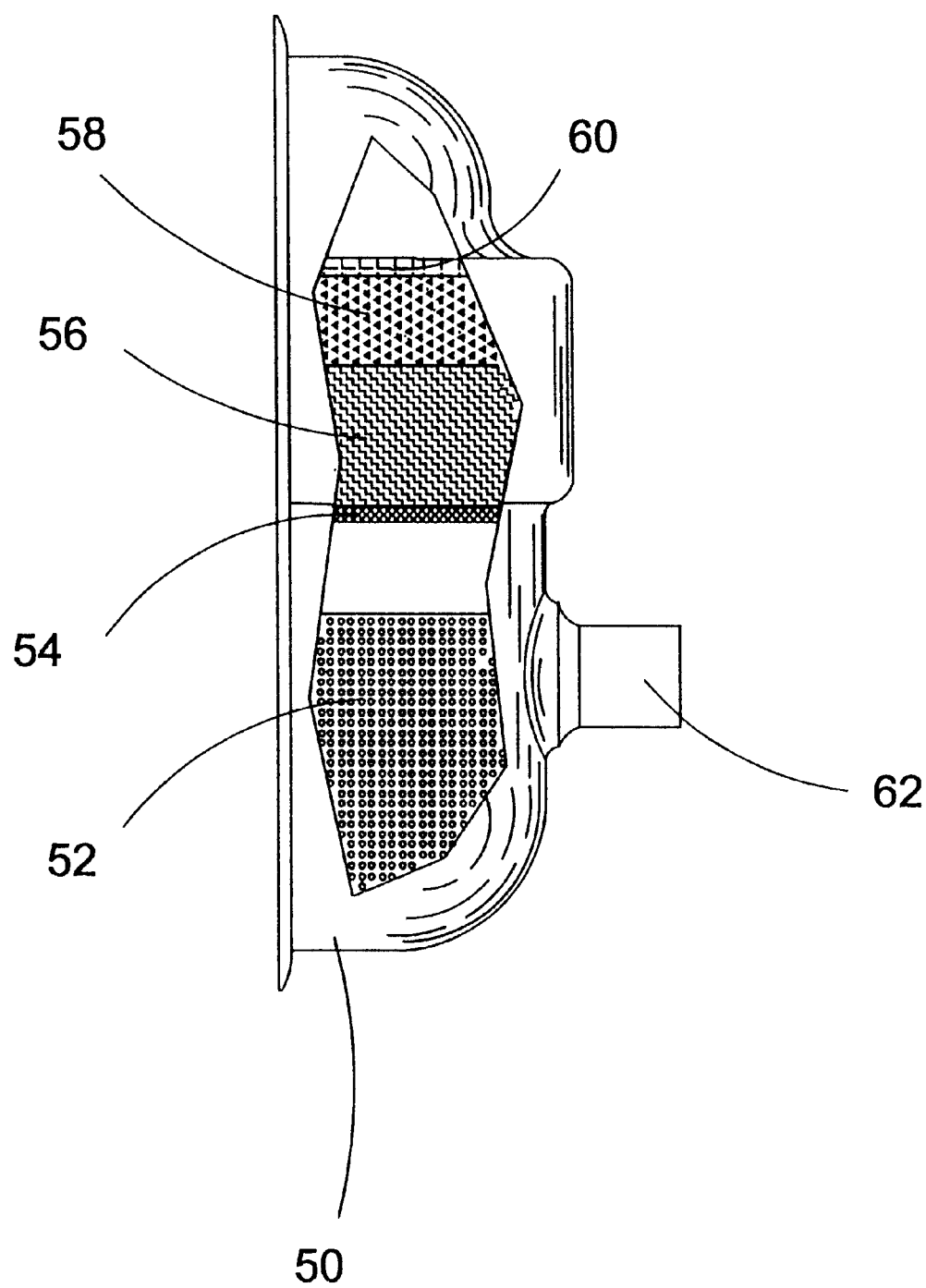
FIG. 5 is a view of the filters and casual liquid collector disposed within the filter housing.

The elongated unitary holder has a proximal end 18 and a distal end 20. The holder is molded to have an upper U-shaped cradle 22, best shown in FIG. 4, which may receive a side of the device. A first end 22a of the cradle 22 is adjacent the proximal end 18 of the holder, and the second end is spaced inwardly of the distal end 20 of the holder. The unitary holder is further provided with a conically shaped portion 24 adjacent the second end of the cradle. The conical portion has a large diameter end 24a, and a small diameter portion 24b, the small diameter portion being nearer the distal end 20. A piercable membrane 26 is molded into the small diameter distal end portion 24b of the conical portion, and this membrane may be pierced by an electrode of an electrically powered cauterization pencil when it is inserted into the conical portion, thus providing a leak barrier. An elongated tubular opening 28 is molded into the holder adjacent the distal end as can best be seen from FIG. 3. When a cauterization pencil is carried by the pencil holder, the electrode 30 will be disposed adjacent the top of the opening 28. As can be seen the tubular opening is angled downwardly and is in fluid communication with an oval shaped lumen 32 which is disposed below the cradle 22 and the conical portion 24. In order to maintain a proper fluid flow of surgical smoke and aerosol from the opening at the distal end of the pencil holder, a relatively thick portion 34 is provided between the conical portion and the lumen 32. (The thick portion is provided with suitable transversely extending apertures 35.) The holder 16 may be provided with a slit (not shown) extending from the membrane 26 to the distal end, the slit being above the opening 28. The purpose of the slit is to facilitate the changing of electrodes 30 in a cauterization pencil 12.

Figure 7:
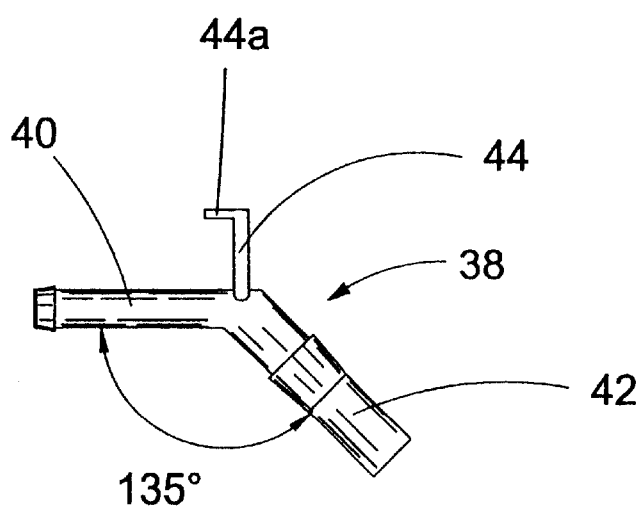
FIG. 7 is a view of the tubular substantially rigid back end piece shown in FIG. 1.
Figure 7A:
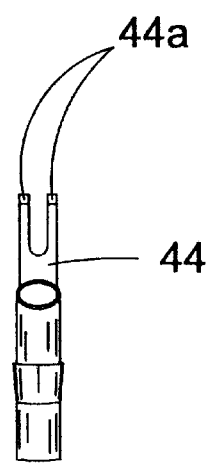
FIG. 7A is an end view of FIG. 7.

The lumen 32 is connected to a suction tube 36 by a tubular substantially rigid back end piece 38 in FIG. 7. The back end piece 38 has first and second tubular portions 40, 42, which are disposed at an angle of 135° to each other. The back end piece is further provided with an intermediate retaining element in the form of a fork 44 which has overhanging spaced apart ears 44a. The retaining fork is located midway between the two tubular portions 40, 42. Each of the tubular portions are provided with suitable barbs 46. When the parts are assembled, the tubular portion 40, which has an oval cross-section as can best be seen from FIG. 7A, is inserted into the lumen 32 until the proximal end is adjacent the fork 44. The suction tube 36 is formed from corrugated tubing which will resist kinking. As can be seen from FIG. 1A, one end of the tubing 36 is telescoped over the tubular portion 42 in a fluid tight manner.

As can be seen from FIG. 2 the length $D_1$, of the pencil 12 from its proximal end 12p to the end of the conical portion 12c is greater than the length $D_2$ of the cradle portion 22 and the conically shaped portion. Thus, when the pencil is inserted into the holder, the electrode will pierce the membrane 26, and the conical leading edge of the pencil will be snugly received in the conical portion. However, it will still be necessary to stretch the holder so that the forks 44 can engage the rear end of the pencil, the overhanging ears 44a holding it in place. While an electrosurgical pencil 12 is illustrated, other devices will be held in the same manner.

Figure 6:
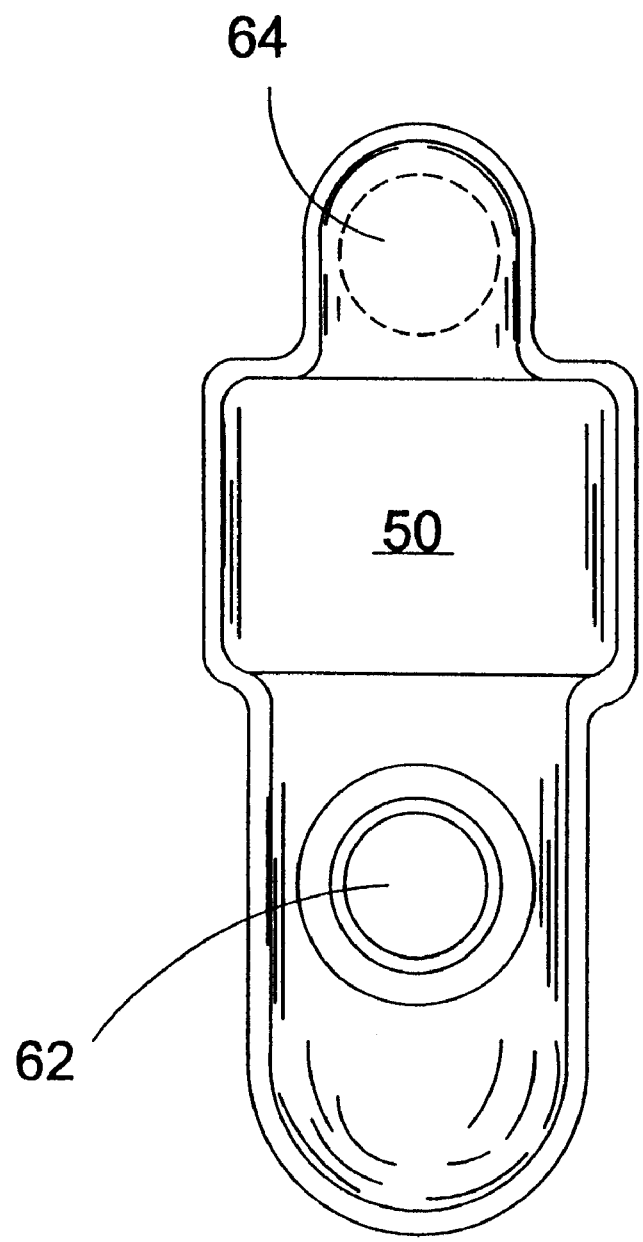
FIG. 6 is an end view of the filter housing shown in FIG. 5.

In the illustrated embodiment, the electrical leads 14 pass through the fork 44 and enter into the suction tube 36 adjacent the plastic back end piece. Alternatively, the leads may enter the back end piece. While a single lead is shown, several leads may be employed, which leads will be suitably coupled together. Alternatively, the leads may be molded into the suction tube. The leads exit the suction tube adjacent a filter housing 50. Within the filter housing 50 a four stage filter and a casual liquid collector are provided. Thus, the filter housing contains a casual liquid collector 52, a pre-filter 54, an ULPA filter material 56, a charcoal filter 58, and a fines filter 60. The casual liquid collector 52 may be an absorbent sheet having an absorbency of 2–3 $gm/in^2$. In the illustrated embodiment, the collector 52 has a surface area of about 3 $in^2$ and may capture 7–10 ml of fluid. Such a sheet material is available from Safetec of America under the product name of Zorb Sheet 4400 Series. The end of the suction tube 36 is telescoped over a tubular projection 62 on the filter housing in an air tight manner. Similarly, in the illustrated embodiment, the aperture 64 (shown in FIG. 6) receives a tubular projection 66 on a vacuum source such as a vacuum smoke evacuation unit 68. While a vacuum smoke evacuation unit is shown, it should be noted that the suction tube may be connected directly to a hospital smoke plume evacuation system.

As previously noted, the back end piece has the tubular portions disposed at an angle of 135° to each other. This is to insure that the electrical lead and the suction tube will lay over the user's wrist, and not interfere with his field of view. Also, by having the electrical lead pass through the suction tube, wires and tubes are minimized in the field of use.

While a preferred form of this invention has been described above and shown in the accompanying drawings, it should be understood that applicant does not intend to be limited to the particular details described above and illustrated in the accompanying drawings, but intends to be limited only to the scope of the invention as defined by the following claims.

What is claimed is:

1. A smoke evacuation apparatus adapted to receive and hold a surgical device which may produce smoke, the device having proximal and distal ends, and which apparatus can be connected to a suction tube; the apparatus comprising:

an elongated unitary holder formed of elastic material for receiving a device, the unitary holder having proximal and distal ends and including an upper U-shaped cradle having a first end at the proximal end of the unitary holder and a second end spaced inwardly of the distal end of the unitary holder, a conically shaped portion for capturing a distal end portion of a device, the conically shaped portion being spaced inwardly of the distal end of the unitary holder, the conically shaped portion having a large diameter proximal end adjacent the distal end of the cradle and a small diameter distal end, an oval shaped lumen located adjacent the cradle and the conically shaped portion, and an elongated tubular opening at the distal end of the unitary holder through which smoke may pass; and a tubular substantially rigid back end piece provided with a proximal end portion, a distal end portion, and an intermediate retaining element which may bear against the proximal end of a device, the distal end portion of the back end piece being snugly received within the oval shaped lumen of the unitary holder, and the proximal end portion of the back end piece being adapted to be connected to a suction tube;

the unitary holder being elastically stretched when the parts are assembled to cause the device to be retained between the conically shaped portion and the retaining element, smoke to be evacuated passing through the elongated tubular opening, the oval shaped lumen, and the tubular back end piece to a suction tube.

2. The smoke evacuation apparatus as set forth in claim 1 wherein the retaining element is a fork, the surgical device having an electrical lead, the lead adapted to pass through the fork.

3. The smoke evacuation apparatus as set forth in claim 1 wherein the surgical device which may produce smoke is a cauterization pencil having an electrode, and wherein a membrane is formed in the in the small diameter distal end of the conically shaped portion which may be pierced by the electrode of a cauterization pencil when it is inserted, thus providing a leak barrier.

4. A smoke evacuation apparatus shaped to receive and hold a surgical device which may produce smoke, the device having proximal and distal ends and a power source, and which smoke evacuation apparatus can be connected to a vacuum source; the apparatus comprising:

an elongated unitary device holder formed of elastic material, the unitary device holder having proximal and distal ends and including an upper U-shaped cradle having a first end at the proximal end of the holder and a second end spaced inwardly of the distal end of the holder, a conically shaped portion for capturing a distal end portion of the device, the conically shaped portion being spaced inwardly of the distal end of the holder and adjacent the distal end of the cradle, the conically shaped portion having a large diameter opening adjacent the distal end of the cradle and a small diameter distal end, an oval shaped lumen located adjacent the cradle and the conically shaped portion, and an elongated tubular opening at the distal end of the holder through which smoke may pass;

a suction tube; and a tubular substantially rigid back end piece connecting the oval shaped lumen of the holder to the suction tube, the tubular back end piece being provided with a retaining element which is adapted to bear against the proximal end of the device, the distal end of the device adapted to be snugly received within the conically shaped portion, the elastic holder being elastically stretched when the parts are assembled to cause the device to be retained between the conically shaped portion and the retaining element, smoke to be evacuated passing through the elongated tubular opening, the oval shaped lumen, the tubular back end piece, and the suction tube, the power source for the device being captured by the suction tube.

5. The smoke evacuation apparatus as set forth in claim 4 wherein the tubular substantially rigid back end piece is formed at an angle of about 135° to cause the suction tube and power source to lay comfortably over the user's wrist.

6. The smoke evacuation apparatus as set forth in claim 4 wherein the power source for the device is adapted to pass through the suction tube, the power source adapted to enter the suction tube adjacent one end and adapted to exit the suction tube adjacent the other end.

7. A combined smoke evacuation and filter apparatus shaped to receive and hold a surgical device which may produce smoke, which devices have proximal and distal ends and may be powered through a power source such as an electrical lead or air line, and which apparatus which can be connected to a vacuum source; the apparatus comprising:

an elongated unitary holder for receiving a device, the holder being formed of elastic material, the unitary holder having proximal and distal ends and including
a U-shaped device cradle which extends from the proximal end of the holder,
a conically shaped portion adjacent the distal end of the cradle,
an oval shaped lumen located just below the cradle and the conically shaped portion, and
an elongated tubular opening at the distal end of the holder through which smoke may pass;

a suction tube;

a tubular back end piece connecting the oval shaped lumen of the holder to the suction tube; and a filter housing at an end of the suction tube, which filter housing may be connected to a vacuum source so that smoke and other debris may be vacuumed into the elongated tubular opening at the distal end of the unitary holder, through the lumen, through the tubular back end piece, through the suction tube, and then through the filter housing, the filter housing including one or more filters.

8. The combined smoke evacuation and filter apparatus as set forth in claim 7 wherein the tubular back end piece is provided with a retaining element which is adapted to bear against the proximal end of the device, the distal end of the device adapted to be snugly received within the conically shaped portion, the elastic device holder being elastically stretched when the parts are assembled to cause the device to be retained.

9. The combined smoke evacuation and filter apparatus as set forth in claim 7 wherein suction tube is adapted to carry the power source of the device.

10. The combined smoke evacuation and filter apparatus as set forth in claim 9 wherein the power source is adapted to pass through the suction tube, the lead for the device adapted to enter the suction tube adjacent the back end piece and adapted to exit the suction tube adjacent the filter housing.

11. The combined smoke evacuation and filter apparatus as set forth in claim 7 wherein the filter housing contains a four stage filter and a casual liquid collector.

12. The combined smoke evacuation and filter apparatus as set forth in claim 11 wherein the casual liquid collector is disposed below the four stage filter when the filter housing is connected to the vacuum source.

13. The combined smoke evacuation and filter apparatus as set forth in claim 7 wherein the tubular back end piece is formed of substantially rigid plastic at an angle of about 135° to cause the suction tube to lay comfortably over the user's wrist.

14. The combined smoke evacuation and filter apparatus as set forth in claim 7 wherein a membrane is formed in the in the small diameter distal end of the conically shaped portion and may be pierced by an electrode of a cauterization pencil when it is inserted, thus providing a leak barrier.

15. The combined smoke evacuation and filter apparatus as set forth in claim 7 wherein the apparatus is designed for a single use.

16. The combined smoke evacuation and filter apparatus as set forth in claim 7 wherein the tubular opening is angled downwardly.

17. A combined smoke evacuation and filter apparatus adapted to receive and hold a surgical device which may produce smoke such as a cauterization pencil, which device has proximal and distal ends and may be connected to a source of electrical power through an electrical lead, which apparatus is designed for a single use and may be connected to a vacuum source; the apparatus comprising:

an elongated unitary holder for receiving a device, which holder is formed of an elastic material, the unitary holder having proximal and distal ends and including
an upper U-shaped cradle having a first end at the proximal end of the holder, the cradle having a second end spaced inwardly of the distal end of the pencil holder,
a conically shaped portion spaced inwardly of the second end of the holder and adjacent the distal end of the cradle, the conically shaped portion having a large diameter proximal end adjacent the distal end of the cradle and a small diameter distal end,
a membrane formed in the small diameter distal end of the conically shaped portion which may be pierced by an electrode of a cauterization pencil when it is inserted, thus providing a leak barrier,
an oval shaped lumen located just below the cradle and the conically shaped portion, and
an elongated tubular opening at the distal end of the unitary holder through which smoke may pass, the tubular opening being angled downwardly;

a suction tube, the electrical lead for the device adapted to be captured by the suction tube;

a tubular substantially rigid back end piece connecting the oval shaped lumen of the holder to the suction tube, the tubular back end piece being provided with a retaining element which is adapted to bear against the proximal end of the device, the distal end of the device adapted to be snugly received within the conically shaped portion, the elastic holder being elastically stretched when the parts are assembled to cause the device to be retained, the tubular substantially rigid back end piece being formed at an angle of about 135° to cause the suction tube to lay comfortably over the user's wrist; and a filter housing at an end of the suction tube, the filter housing containing a four stage filter and a casual liquid collector, which filter housing may be connected to a vacuum so that smoke and other debris may be vacuumed into the elongated tubular opening at the distal end of the unitary holder, through the lumen, through the tubular back end piece, through the suction tube, and then through the filters.

* * * * *